United States Patent [19]

Sigl

[11] Patent Number: 4,867,831

[45] Date of Patent: Sep. 19, 1989

[54] METHOD FOR LOTIONED TISSUE PLY ATTACHMENT

[75] Inventor: Wayne C. Sigl, Neenah, Wis.

[73] Assignee: Kimberly-Clark Corporation, Neenah, Wis.

[21] Appl. No.: 265,730

[22] Filed: Nov. 1, 1988

Related U.S. Application Data

[60] Division of Ser. No. 124,635, Nov. 24, 1987, Pat. No. 4,806,418, which is a continuation of Ser. No. 895,074, Aug. 11, 1986, abandoned.

[51] Int. Cl.$^4$ .................... B32B 31/04; B32B 31/20
[52] U.S. Cl. .................... 156/283; 156/210; 156/219; 156/291; 156/292
[58] Field of Search ............. 428/154, 166, 198, 172, 428/206, 211, 284; 156/199, 209, 210, 219, 291, 292, 582, 283, 284; 128/156; 118/688

[56] References Cited

U.S. PATENT DOCUMENTS

| | | | |
|---|---|---|---|
| 3,654,020 | 4/1972 | Robinson | 156/291 |
| 3,682,238 | 8/1972 | Smith | 156/291 |
| 4,189,896 | 2/1980 | Kolbach | 118/44 |
| 4,481,243 | 11/1984 | Allen | 428/154 |
| 4,561,380 | 12/1985 | Mulder | 118/688 |

*Primary Examiner*—Merrell C. Cashion, Jr.
*Attorney, Agent, or Firm*—Gregory E. Croft

[57] ABSTRACT

Ply attachment for multiply lotioned tissue products is accomplished by distributing thermoplastic particles between the plies and melting the thermoplastic particles to bond together the fibers of the two plies.

7 Claims, No Drawings

METHOD FOR LOTIONED TISSUE PLY ATTACHMENT

This is a divisional of Ser. No. 07/124,635 filed Nov. 24, 1987, now U.S. Pat. No. 4,806,418, which is a continuation of Ser. No. 06/895,074 filed Aug. 11, 1986, now abandoned.

In the manufacture of facial tissue, two-ply products are typically held together by crimping the edges of the two plies. However, recently some products have been developed which contain lotions or other ingredients which act to inhibit ply attachment by crimping. For example, U.S. Pat. No. 4,481,243 to Allen describes a lotioned tissue product which is designed to sooth the user's skin. Because the lotion prevents successful edge crimping, the lotion is applied only to areas of the tissue which are not to be crimped, namely the center of the tissue. This of course leaves areas of the tissue which are untreated and are potentially irritating to the user.

Therefore there is a need for a method of ply attachment which is not sensitive to the ingredients contained within treated tissues.

SUMMARY OF THE INVENTION

In general, the invention resides in a method for attaching together two plies of tissue, such as facial and bath tissue and the like, comprising: (a) distributing thermoplastic particles over one surface of a first tissue ply; (b) bringing a second tissue ply into contacting relationship with the thermoplastic particle-containing surface of the first tissue ply; (c) melting or softening the thermoplastic particles; and (d) solidifying the melted or softened thermoplastic particles whereby the first and second tissue plies become bonded together. Although this method can be used to attach together two or more plies of any tissue, it is particularly advantageous for attaching together tissue plies wherein one or both of the plies contain ingredients such as emollients, lotions, oils, and the like, the presence of which prevents attachment by crimping. For purposes herein, these various ingredients are lumped together into the single term "lotion."

The thermoplastic particles can be distributed over the surface in any desired pattern, although a light overall dusting of one ply is preferred for convenience. A suitable means for distributing the particles is described in U.S. Pat. No. 4,561,380 to Mulder et al., which is incorporated herein by reference. However, it is within the scope of this invention that the thermoplastic particles be distributed on or within the ply or plies in any suitable manner, such as by incorporating the particles into the furnish and forming the plies with the thermoplastic particles contained therein. Alternatively the thermoplastic particles can be applied to the surface of one or both plies at distinct spaced-apart spots or in a line pattern.

In order for ply attachment (bonding) to occur, the second ply must be brought into a contacting relationship with the thermoplastic particle-containing surface of the first ply. The necessary contact, heating, and cooling is most easily accomplished in a heated nip, in which the thermoplastic particles are melted or otherwise sufficiently softened and cooled to bond the plies together. Because the molten thermoplastic envelops the individual fibers of both plies, upon hardening the two plies become bonded together. As such this method is effective regardless of the presence of fiber coatings which would otherwise prevent intra-fiber chemical bonding. Although a heated nip is the most convenient method of achieving ply attachment in accordance with this invention, other means of melting the thermoplastic polymer are also within the scope of this invention, such as the use of ultrasonic bonding or radio frequency sealing.

The particular thermoplastic polymers preferred for use in the method of this invention are polyethylene and polypropylene because of their availability and low cost. However, any thermoplastic polymer is suitable from a purely technical standpoint. The particle size of the thermoplastic particle is of some importance in that the particles must be small enough to avoid adverse effects on the perceived softness of the tissue product. In general, the thermoplastic particles should be small enough to pass through a 20 mesh screen. Particles larger than 20 mesh can be detected in the tissue. In addition, when larger particles are present, the melted thermoplastic may penetrate the tissue web and cause blocking when the web is wound onto a roll. (For purposes herein, mesh size is as defined in ASTM D-1921.) A suitable form of thermoplastic particle is commercially available under the name "Microthene" from U.S.I. Corporation. This product is available in different grades of a very fine polyolefin powder having different mesh sizes.

For facial tissue, the particle distribution over the surface of the first ply should be less than about 0.0025 grams per square inch in order to avoid an overly stiff product. The particle density will depend greatly on the particle size and the desired bond strength between the plies. A particle density of about 0.0006 grams per square inch or les is preferred for facial and bath tissue, but in any particular case the particle density will depend upon the nature of the product and its intended use. Heavier basis weight products, such as wipes and paper towels, may need stronger ply attachment and can use higher particle densities because any resulting increase in stiffness is less noticeable or critical.

EXAMPLES

In order to further illustrate the method of this invention, a commercially available lotion-treated ply of facial tissue was dusted with a low density polyethylene powder. The lotion contained mineral oil, cetearyl alcohol, and steareth-2 and was present in the ply at a level of about 12 percent by weight. The polyethylene powder was Microthene MN714, which is a 50 mesh material. The powder was evenly distributed over the surface of the lotion-treated tissue using a small shaker tray. A second lotion-treated ply was laid on top of the first and briefly compressed with a heated laboratory iron (280° F. surface temperature). The iron caused the polyethylene powder to melt and bind the two plies together. This procedure was repeated for the following powder densities (grams per square inch): 0.000625, 0.00125, 0.0025, 0.00625, 0.0125 and 0.01875. In all cases the ply bonding was strong enough to tear the plies when separated, even at the lowest level of powder addition, illustrating the effectiveness of this method.

It must also be pointed out that the method of this invention can be utilized to produce multiply tissue products wherein the lotion is applied simultaneously with the thermoplastic particles. For example, encapsulated lotions are available in microbead form which can be applied to the tissue with the thermoplastic bonding particles. In this case, the lotion is released when the two plies are bonded together.

It will be appreciated that the foregoing examples, shown for purposes of illustration, are not to be construed as limiting the scope of this invention.

I claim:

1. A method for attaching together two plies of tissue wherein at least one of said tissue plies contains lotion, said method comprising:
   (a) distributing less than about 0.0025 grams of thermoplastic particles per square inch over one surface of a first tissue ply;
   (b) bringing a second tissue ply into contacting relationship with the thermoplastic particle-containing surface of the first tissue ply;
   (c) melting or softening the thermoplastic particles; and
   (d) solidifying the melted or softened thermoplastic particles, whereby the first and second tissue plies become bonded together where lotion is present.

2. The method of claim 1 wherein the first tissue ply contains lotion and the second tissue ply does not contain lotion.

3. The method of claim 1 wherein the second tissue ply contains lotion and the first tissue ply does not contain lotion.

4. The method of claim 7 wherein the first and second tissue plies both contain lotion.

5. The method of claim 1 wherein the solidified thermoplastic particles are distributed evenly over the surface of the first ply.

6. The method of claim 5 wherein the particle distribution over the surface of the first ply is less than about 0.0006 grams per square inch.

7. The method of claim 6 wherein the thermoplastic particles are polyethylene.

* * * * *